US00PP37416P3

(12) United States Plant Patent
Olesen

(10) Patent No.: US PP37,416 P3
(45) Date of Patent: May 12, 2026

(54) MINIATURE ROSE PLANT NAMED 'POULTY046'

(50) Latin Name: *Rosa hybrida*
Varietal Denomination: Poulty046

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/831,808

(22) Filed: Sep. 15, 2025

(65) Prior Publication Data

US 2026/0083035 P1 Mar. 19, 2026

(30) Foreign Application Priority Data

Sep. 19, 2024 (QZ) ..... PBR 2024/2195

(51) Int. Cl.
*A01H 5/02* (2018.01)
*A01H 6/74* (2018.01)

(52) U.S. Cl.
USPC ..... Plt./122
CPC ..... *A01H 6/749* (2018.05); *A01H 5/02* (2013.01)

(58) Field of Classification Search
USPC ..... Plt./122
CPC ..... A01H 6/749; A01H 5/02
See application file for complete search history.

*Primary Examiner* — Keith O. Robinson

(57) ABSTRACT

A new garden rose plant of the miniature class which has abundant, red-purple flowers and dark green foliage. This new and distinct variety has shown to be uniform and stable in the resulting generations from asexual propagation.

1 Drawing Sheet

Botanical designation: *Rosa hybrida.*

Variety denomination: 'Poulty046'.

This application claims priority to Plant Breeder's Rights Application Number 2024/2195, which was filed at the Community Plant Variety Rights Office in the European Union on Sep. 19, 2024, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2018 and the resulting seeds were planted in a controlled environment in Odense, Denmark. The new variety, named 'Poulty046', originated as a single seedling from the stated cross.

The new variety may be distinguished from its male pollen parent and female seed parent primarily by the following characteristics. The male pollen parent plant has a petal count of about 40 petals while the new variety has a flower petal count of about 106. The female seed parent plant has red-purple flowers with about 30 petals, while the new variety has red-purple flowers with a much larger petal count of 106.

The objective of the hybridization of this rose variety was to create a new and distinct variety with unique qualities, such as:

1. Uniform and abundant red-purple flowers with high petal count and a long stable shelf-life;

2. Vigorous, but compact growth when propagated on its own roots;
3. Suitability for commercial production in small containers; and
4. Exceptional disease resistance.

This combination of qualities is not present in previously available commercial cultivars of this type, known to the inventor, and distinguish 'Poulty046' from all other varieties of which we are aware.

As part of the rose development program, Mogens N. Olesen germinated the seeds from the aforementioned hybridization during winter of 2018 and conducted evaluations on the resulting seedlings in a controlled environment in Odense, Denmark. 'Poulty046' was selected in the spring of 2019 by the inventor as a single plant from the progeny of the aforementioned hybridization.

Asexual reproduction of 'Poulty046' by rooted cuttings was first done by Mogens N. Olesen in the nursery in Odense, Denmark in July 2019. This initial and other subsequent asexual propagations conducted in controlled environments have demonstrated that the characteristics of 'Poulty046' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulty046'.

Specifically illustrated in the drawing are a cluster of flower buds on the branch, a bare stem exhibiting prickles, mature and juvenile leaves, an open flower, petals detached revealing reproductive flower parts, and sepals detached showing receptacle shape. Plants shown are 3 months old.

DETAILED DESCRIPTION OF THE VARIETY

The following is a description of 'Poulty046', as observed in its growth in a glasshouse nursery in Odense Denmark. Observed plants are 3 months of age, and were grown on their own roots in 17 cm pots. Color references are made using The Royal Horticultural Society (London, England) Colour Chart, 2001, except where common terms of color are used.

For a comparison, several physical characteristics of the rose variety 'Poulty027', U.S. Plant Pat. No. 34,808, are compared to the claimed plant. For 'Poulty027' open flowers are Red Group 52B becoming Red-Purple Group 58B at maturity. For 'Poulty046' open flowers are Red-Purple Group 61C. While the comparison variety has moderate undulations of the petal margins, the claimed plant has strong undulations in the petal margins. Flower petal count for the claimed plant is 106, while the comparison variety has about 35 flower petals.

FLOWER AND FLOWER BUD

Blooming habit: Continuous.

Flower bud:

- *Size.*—Upon opening, 24 mm in length from base of receptacle to end of bud. Bud diameter is 12 to 15 mm.
- *Bud form.*—Globose.
- *Bud color.*—As sepals divide petals are Red-Purple Group 60B and Red-Purple Group 61C.
- *Sepal inner surface.*—Color: Yellow-Green Group 146D. Surface: Lightly pubescent.
- *Sepal outer surface.*—Color: Yellow-Green Group 144A. Texture: Smooth.
- *Sepal shape.*—Apex: Cirrhose. Base: Flat at union with receptacle.
- *Sepal margin.*—Margins have weak foliaceous appendages on three of the five sepals.
- *Sepal size.*—About 22 mm long, 8 mm wide.
- *Receptacle.*—Texture: Smooth. Size: 7 mm in height, 8 mm wide. Color: Yellow-Green Group 144A. Shape: Funnel.
- *Pedicel.*—Surface: Somewhat rough with stipitate glands. Length: About 36 mm. Diameter: 2.5 mm on average. Color: Yellow-Green Group 144A. Strength: Strong.
- *Peduncle.*—Length: 7 mm to 80 mm. Diameter: About 3 mm. Color: Yellow-Green Group 144A. Texture: Smooth. Strength: Strong.

Flower bud development: Flower buds are borne in clusters of 4 to 7 flower buds per stem. Arrangement similar to a corymb.

Flower bloom:

- *Fragrance.*—Light rose floral-like scent, to none.
- *Duration.*—The blooms have a duration on the plant of approximately 21 days. Petals fall cleanly away from plant after flowers have fully matured.
- *Size.*—Flower diameter is about 45 mm when open. Flower depth is 15 mm.
- *Flower shape.*—Quartered-rosette, very double, with many overlapping petals packed into quarter sections.
- Shape of flower, side view.—The upper and lower portions are flat.

Petalage: Under normal conditions, flowers have about 106 petals.

General tonality of flower: Open flowers are Red-Purple Group 61C.

Petal color:

- *Upon opening, outer petals.*—Upper surface: Red-Purple Group 61C. Occasionally streaks of Green-White Group 157A. Lower surface: Red-Purple Group 60D blended with Greyed-Purple Group 186B.
- *Upon opening, inner petals.*—Upper surface: Red-Purple Group N57A. Lower surface: Red-Purple Group 61C.
- *Basal petal spots, upon opening.*—Upper surface: Green-White Group 157A. Lower surface: Green-White Group 157A
- *After opening, outer petals.*—Upper surface: Red-Purple Group 61B and Red-Purple Group N57A blended. Lower surface: Blend of Red-Purple Group 61C and 61D.
- *After opening, inner petals.*—Upper surface: Red-Purple Group N57A. Lower surface: Red-Purple Group 61C.
- *Basal petal spots, after opening.*—Upper surface: Lower surface: Yellow Group 8B.

Petals:

- *Petal reflex.*—Not reflexed.
- *Margin.*—Highly irregular with numerous clefts and lobes. There is a point at the center of the apex. No undulations.
- *Shape.*—Broad and elliptic. Apex shape: Rounded. Base shape: Acute.
- *Size.*—About 20 mm (l)×25 mm (w).
- *Texture.*—Smooth.
- *Thickness.*—Average.

Petaloids:

- *Size.*—4 mm (l) by 4 mm (w).
- *Quantity.*—About 35.
- *Shape.*—Elliptical with an acute base and rounded apices.
- *Color.*—At the basal point of attachment Yellow Group 8B. Red-Purple Group N57A on the upper surface. The lower surface is Red-Purple Group 61C.

Reproductive flower parts:

- *Pollen.*—None observed.
- *Anthers.*—Size: 2 mm in length. Color: Yellow Group 8C. Quantity: 40 on average.
- *Filaments.*—Color: Yellow Group 6C. Length: 2 mm.
- *Pistils.*—Length: 3 mm. Quantity: 28 on average.
- *Stigmas.*—Color: Yellow-White Group 158A.
- *Styles.*—Color: Yellow-White Group 158A.
- *Location of stigmas.*—Level in location relative to the length of the filaments and the height of the anthers.
- *Hips.*—None Observed.

PLANT

Plant growth: Upright, very compact. Plants are about 21 cm in height, and 28 cm wide.

Stems:

- *Color of juvenile growth.*—Yellow-Green Group 144B.
- *Color of mature growth.*—Yellow-Green Group 144A.

*Length*.—Canes are about 15 cm from the base of the plant to the flowering portion.

*Diameter*.—About 4 mm.

*Internodes*.—On mature canes about 20 mm between nodes.

*Surface texture*.—Young wood: Smooth. Older wood: Rough with prickles.

Long prickles:

*Incidence*.—About 7 prickles per 10 cm of stem.

*Size*.—Average length of prickles on mature stems is 5 mm.

*Shape*.—Upper portion is linear. Lower portion is linear.

*Color*.—Juvenile prickles: Greyed-Red Group 181C. Mature prickles: Greyed-Red Group 181C.

Plant foliage:

*Compound leaf*.—About 85 mm (l)×52 mm (w).

*Quantity*.—3 to 4 leaves per 10 cm of stem on average.

*Leaf bearing angle to the stem*.—90 degrees.

*Color of juvenile foliage*.—Upper side: Yellow-Green Group 146A. Lower side: Yellow-Green Group 147B.

*Color of mature foliage*.—Upper side: Yellow-Green Group 147A. Lower side: Yellow-Green Group 147B.

Plant leaves and leaflets:

*Stipules*.—Size: 10 mm long, 3 or 4 mm wide. Quantity: 2 per compound leaf. Shape: Linear, slightly broad based with outward extending apices. Margins: Finely serrated. Color: Yellow-Green Group 144A.

*Petiole*.—Length: Average 21 mm. Diameter: 1 mm. Upper surface color: Yellow-Green Group 144A. Lower surface color: Yellow-Green Group 144A.

*Rachis*.—Length: About 28 mm. Upper surface color: Yellow-Green Group 144A. Lower surface color: Yellow-Green Group 144A.

*Leaflet*.—Quantity: Normally 7 leaflets. Margins: Serrated. Size: Terminal leaflets are about 36 mm long, 18 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulty046' substantially as described and illustrated herein.

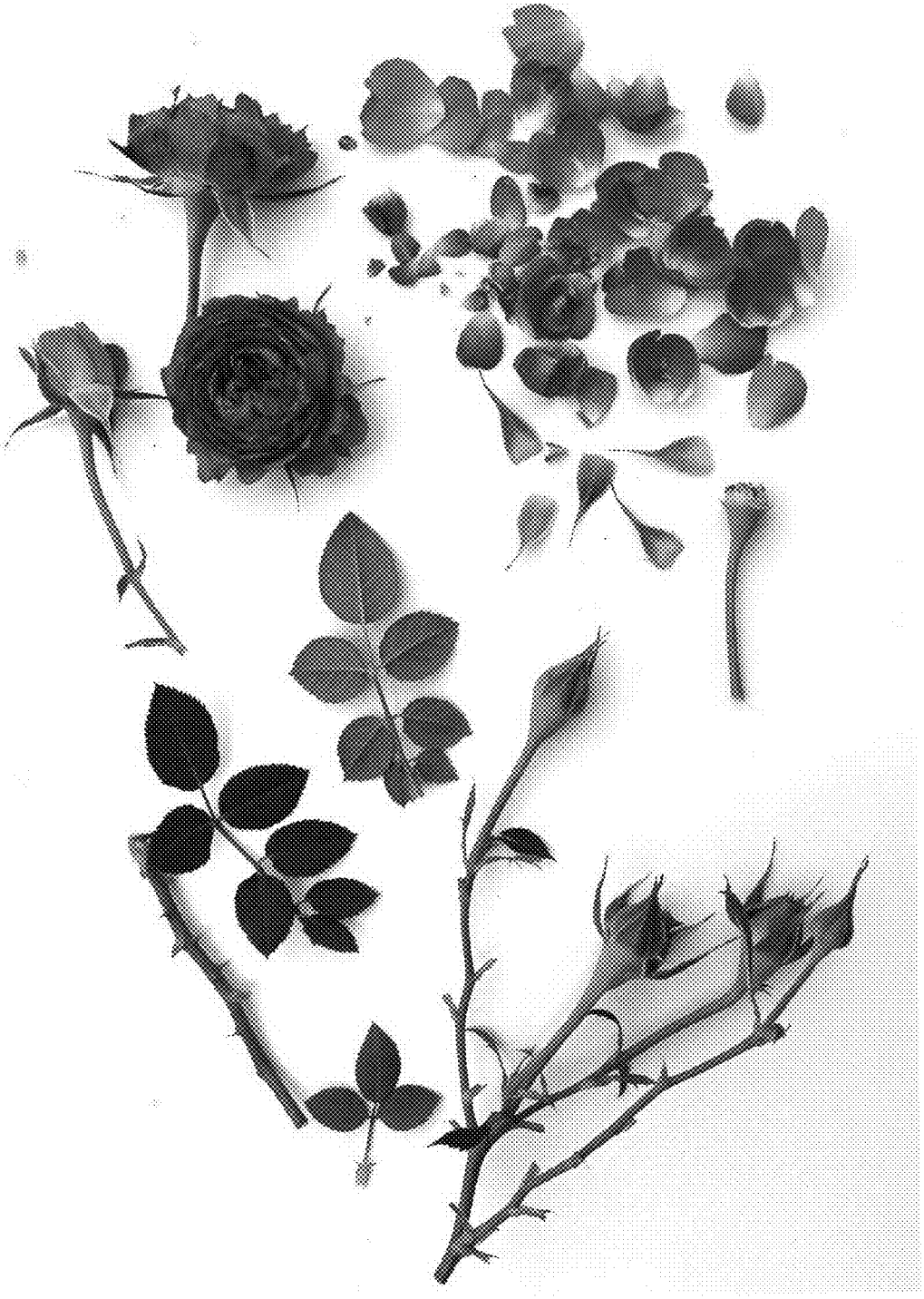

* * * * *